United States Patent [19]

Triplett

[11] Patent Number: 5,183,759

[45] Date of Patent: Feb. 2, 1993

[54] RECOMBINANT RHIZOBIUM BACTERIA INOCULANTS

[75] Inventor: Eric W. Triplett, Madison, Wis.

[73] Assignee: Wisconsin Alumni Research Foundation, Madison, Wis.

[21] Appl. No.: 707,245

[22] Filed: May 22, 1991

Related U.S. Application Data

[63] Continuation of Ser. No. 358,744, May 30, 1989, abandoned.

[51] Int. Cl.$^5$ .................... C12R 1/41; C12P 21/00; C12P 21/04; C12N 15/00
[52] U.S. Cl. .................... 435/252.2; 435/69.1; 435/71.3; 435/172.3; 435/252.3; 435/878; 71/7
[58] Field of Search .................. 435/252.2, 252.3, 878, 435/69.1, 71.3, 172.3; 47/57.6, DIG. 9; 71/7; 800/200

[56] References Cited

FOREIGN PATENT DOCUMENTS 242474 10/1987 European Pat. Off. .
245931 11/1987 European Pat. Off. .
263553  4/1988 European Pat. Off. .

OTHER PUBLICATIONS

Triplett et al. 1987, Plant Physiology 85: 335-342.
Ditta, G. Methods Enzymol. 18: 519-528 (1986).
Acuna et al. 1987, Plant Mol. Biol. 9: 41-50.
E. Triplett, 85 P.N.A.S. USA 3810-3814 (Jun. 1988).
E. Triplett, 56 App. Env. Microb. 98-103 (1990).
D. Borthakur et al., 105 Chem. Abst. #92239x, p. 165 (1986).
P. Muriana et al., 83 Biol. Abst., #117524 (1987).
E. Triplett et al., Biosis: 37 Biol. Abst. 28789 (1988).
E. Triplett et al., 85(2) Biological Abs. #22268 (1988).
Abstract Second Annual ASM Conference On Biotechnology (Jun. 25-28, 1987), E. Triplett.
Abstract GP4 from the North American Rhizobium conference (Aug. 1987), E. Triplett.
A Jun. 26, 1987 news release by the University of California-Riverside reporting on E. Triplett's work.
E. Schwinghamer et al., 64 Arch. Mikrobiol. 130-145 (1968).
A. Hodgson et al., 17 Soil Biol. Biochem. 475-478 (1985).
S. Dowdle et al., 50 Appl. Environ. Microbiol. 1171-1176 (1985).
D. Dowling et al., 40 Ann. Rev. Microbiol. 131-157 (1986).
T. McLoughlin et al., 169 J. Bacteriol. 410-413 (1987).
D. Dowling et al., 169 J. Bacteriol. 1345-1348 (1987).
F. Bergersen, 14 Aust. J. Biol. Sci. 349-360 (1961).
H. Boyer et al., 41 J. Mol. Biol. 459-472 (1969).
J. Beringer et al., 276 Nature 633-634 (1978).
D. Figurski et al., 76 P.N.A.S. USA 1648-1652 (1979).
D. Holmes et al., 114 Anal. Biochem. 193-197 (1981).
R. Roughley et al., in *Nitrogen Fixation in Legumes*, Academic Press 193-209 (1982).
S. Leong et al., 257 J. Biol. Chem. 8724-8730 (1982).
D. Hanahan, 166 J. Mol. Biol. 557-580 (1983).
G. Barry, 4 Bio/Technology 446-449 (1986).
G. Barry, 71 Gene 75-84 (1988).
N. Keen et al., 70 Gene 191-197 (1988).

*Primary Examiner*—David T. Fox
*Attorney, Agent, or Firm*—Quarles & Brady

[57] ABSTRACT

The sequences of a Rhizobium bacteria responsible for competitiveness with respect to plant nodulation have been isolated and permanently transferred to superior nodulating Rhizobium genome. This has resulted in a stable construct that can form a plant inoculant that yields effective nodulation, while reducing the risk of suppression by other bacteria in the environment.

2 Claims, No Drawings

RECOMBINANT RHIZOBIUM BACTERIA INOCULANTS

This invention was made with U.S. government support awarded by the U.S. Dept. of Agriculture (USDA), Grant #(s): 89-37262-4792, 87-CRCR-1-2571 and HATCH Funds. The U.S. Government has certain rights in this invention.

This application is a continuation of application Ser. No. 07/358,744, filed May 30, 1989, now abandoned.

BACKGROUND OF THE INVENTION

1. Field Of The Invention

The present invention relates to recombinant DNA technology. It appears especially useful for improving the nodulation (and thus nitrogen fixation) capability of plants.

2. Description Of The Art

Root nodule Rhizobium bacteria are responsible for symbiotic nitrogen fixation in the nodules of certain plants (e.g. legumes). Where natural bacterial activity is ineffective, the plants must rely on the existing nitrogen in the soil or on fertilizers. Where the former occurs, the quality of the soil is reduced. Where the latter occurs, the cost to the farmer (and ultimately the public) can be substantial. Further, the use of fertilizers often raises environmental concerns.

It is now known that the presence of certain "inferior" strains of Rhizobium in soil can depress the productivity of not only other natural bacteria, but also of "superior" bacteria added by inoculation of seeds. This can frustrate attempts to inoculate seeds prior to planting or to inoculate roots during plant growth. When inoculation has been successful, it is usually because the indigenous bacterial populations have been small.

Many investigators have studied the factors involved in determining nodule occupancy by strains of Rhizobium. See e.g. D. Dowling et al., 40 Annu. Rev. Microbiol. 131-157 (1986) (the disclosure of this article and of all other articles referred to herein are incorporated by reference as if fully set forth). Despite this work, no solutions to the above described Rhizobium competition problem have been developed.

In E. Triplett et al., 85 Plant Physiology 335-342 (1987) and 11th North American Rhizobium Conference Abstract GP4 (1987), my laboratory reported on the fact that the *Rhizobium leguminosarum* bv. *trifolii* bacterial strain T24 appeared to have genes in its coding responsible for a suppressor of other Rhizobium (I named the substance trifolitoxin) and other genes coding for T24's own resistance to trifolitoxin's effects. Unfortunately, I also have found that trifolitoxin production by transconjugant bacterial cells that I had constructed was readily lost in the absence of tetracycline. Thus, the earlier Rhizobium transconjugants were not likely to be able to effectively limit nodulation by trifolitoxin-sensitive indigenous strains of Rhizobium under agricultural conditions (where tetracycline application is impractical).

It was therefore desired to more specifically isolate and characterize the genes responsible for the T24 suppressor and resistance characteristics and use information developed therefrom to find a means for stably inserting such genes in the genome of "superior" Rhizobium so as to ultimately lead to a Rhizobium that can form effective nodules notwithstanding the presence of indigenous strains.

SUMMARY OF THE INVENTION

The invention provides a recombinant Rhizobium bacteria capable of assisting in the formation of nitrogen fixation nodules on at least some plants. The bacteria has a foreign sequence expressibly coding for trifolitoxin. The bacteria preferably also has a sequence coding for resistance to trifolitoxin suppression, with both foreign sequences being in the bacterial genome. The term "genome" is used herein to refer to either the bacterial chromosome or other bacterial genetic sequences in the bacteria.

Inoculants can be provided that use these bacteria. Thus, plant seeds (or the roots of young plants) can be inoculated with the bacteria.

Further, plant cells can be formed that incorporate these sequences (so that the plant strain produces its own trifolitoxin). In the alternative, a production host can produce trifolitoxin on a commercial scale. In either case, the trifolitoxin can be used as a trans inoculant by having the superior strain have the resistance gene only.

It will be appreciated that the invention provide the ability to effectively create nitrogen fixation nodules in the presence of inferior strains.

The objects of the invention therefore include:

A. providing a recombinant bacteria of the above kind;
B. providing a recombinant host of the above kind;
C. providing a plant seed inoculated with a bacteria of the above kind; and
D. providing a plant inoculant using a bacteria of the above kind.

These and still other objects and the advantages of the present invention will be apparent from the description that follows.

DESCRIPTION OF THE PREFERRED EMBODIMENTS

General Overview

*Rhizobium leguminosarum* bv. *trifolii* T24 induces ineffective nodules but produces a potent anti-rhizobial compound, trifolitoxin. As a result of trifolitoxin production, T24 prevents root nodulation by trifolitoxin-sensitive bacterial strains. The main objective of this work was to identify and isolate the trifolitoxin production and resistance genes and permanently transfer those gene to other strains of Rhizobium that produced "superior" nodules.

To achieve this, a genomic library of T24 was prepared in the prior art cosmid vector pLAFR3. One cosmid clone was identified that restored trifolitoxin production and nodulation competitiveness. We formed a recombinant plasmid from this cosmid clone, pTFX1, that conferred trifolitoxin production and resistance on other bacteria (albeit in an unstable fashion).

Transposon mutagenesis and restriction analysis was then used to map and subclone the insert of pTFX1. A 4.4 kb region of DNA, referred to as tfx was found to be necessary for the expression of trifolitoxin production and resistance in Rhizobium. Another portion was found to have sufficient homology to Rhizobium genome to permit the use of a technique for insertion into the genome. Several mutants of pTFX1 (with Tn5 insertions outside the trifolitoxin region) were therefore used to permanently insert the trifolitoxin genes into several strains of Rhizobium. This resulted in a stable construct having the desired characteristics.

METHODS AND MATERIALS

The identification of the precursor cosmid clone, and the formation of plasmid pTFX1 is described in detail in my article, E. Triplett, 85 P.N.A.S. USA 3810–3814 (June, 1988) (not prior art). I then made a restriction map of pTFX1. I did this by restriction analysis of Tn5 insertions in pFFX1. This map was used to determine the size and location of the trifolitoxin genes as well as to develop a strategy to subclone the trifolitoxin genes into the broad host range vector, pRK415, N. Keen et al., 70 Gene 191–197 (1988). I found that the ability of pTFX1 to confer trifolitoxin production as well as resistance in trifolitoxin-sensitive strains of Rhizobium were located within a 4.4 kb region of pTFX1, this knowledge, plus my analysis of the other portions of the insert in turn led to selection of the marker exchange technique for inserting these genes in a bacterial genome.

In my work, Rhizobium strains were cultured at 28° C. on Bergersen's synthetic medium (BSM) as described by F. Bergersen, 14 Aust. J. Biol. Sci. 349–360 (1961). Strains of *E. coli* were cultured at 37° C. on Luria-Bertani (LB) medium. Antibiotics were added as needed at the following final concentrations: kanamycin (Km), 50 ug/ml; tetracycline (Tc), 12.5 ug/ml; spectinomycin (Sp), 50 ug/ml; streptomycin (Sm), 50 ug/ml; gentamycin (Gm), 25 ug/ml; nalidixic acid (Nal), 10 ug/ml; and neomycin (Nm), 75 ug/ml.

Conjugation of the plasmid mutants (e.g. pTFX1::Tn5) into Rhizobium was performed using procedures analogous to those described in E. Triplett et al., 85 Plant Physiol. 335–342 (1987) with some modifications. In this regard, the donor, recipient, and helper strains were mixed in a 1:1:1 ratio in water each at a cell density of approximately $5\times10^7$ per ml. After vortexing, a 5 ul suspension of this mixture is placed on a YM/KB (see E. Triplett (1987), supra) plate with 3% agar. After incubation for two days at 28° C., each mating was resuspended in 0.1 ml water and spread plate on a BSM plate prepared with noble agar and supplemented with tetracycline and streptomycin. The use of noble agar in the interruption media eliminated the background of growth on the plates. After five days, transconjugants were observed.

Conjugations involving the transfer of plasmid DNA between strains of *E. coli* were done as described above except that 5 ul of the mixture of donor, recipient, and helper strains were placed on an LB plate and incubated at 37° C. overnight. Interruptions were done as described above with the appropriate selective media on solid LB medium.

In the transfer of plasmid DNA from *E. coli* to Rhizobium, *E. coli* DH5a (Bethesda Research Labs) (pRK2013), D. Figurski et al., 76 P.N.A.S. USA 1648–1652 (1979), was used as the helper strain. In the transfer of plasmid DNA between two strains of *E. coli, E. coli* HB101, H. Boyer et al., 41 J. Mol. Biol. 459–472 (1969), (pRK2073) (S. Leong et al., 257 J. Biol. Chem. 8724–8730 (1982)) served as the helper strain.

Large scale plasmid preparations were purified by the boiling method described by D. Holmes et al., 114 Anal. Biochem. 193–197 (1981). For restriction analysis of small amounts of plasmid DNA, plasmids were purified from cells grown on sold medium by the alkaline lysis miniprep method described by F. Ausubel et al., Current Protecols In Molecular Biology (1987).

The recombinant plasmid, pTFX1, was mutagenized with Tn5 by the method of G. Ditta, 118 Meth. Enzmol. 519–528 (1986) with slight modifications. The plasmid pTFX1 was transformed into *E. coli* cell line HB101::Tn5 as described by D. Hanahan, 166 J. Mol. Biol. 557–580 (1983) using LB medium supplemented with kanamycin and tetracycline for selection of transformants. The transformants were pooled and conjugated with HB101 (pRK2073) and C2110nal (Ditta, supra). The triparental matings were incubated overnight at 37° C. Cells were resuspended in water and a dilution series plated on LB medium supplemented with kanamycin, tetracycline, and nalidixic acid. Transconjugants were pooled and plasmid DNA isolated by an alkaline lysis miniprep procedure as described by F. Ausubel et al., *Current Protocols In Molecular Biology,* John Wiley & Sons, New York (1987). Fourteen separate matings were performed in order to enhance the prospects of obtaining independent mutations. Plasmid DNA was transformed into *E. coli* DH5a and the subsequent transformants selected on LB medium with kanamycin and tetracycline.

RESTRICTION ANALYSIS

Restriction analysis of three hundred and thirty-six pTFX1::Tn5 mutants was done to provide the information necessary to construct a restriction map of pTFX1. Each mutant was also conjugated into *R. leguminosarum* bv. *trifolii* strain TA1 as described above to determine the trifolitoxin phenotype. (The tfx genes are not expressed in *E. coli.*)

Plasmid DNA of each pTFX1::Tn5 mutant was cleaved with the following restriction enzymes: Eco RI, Kpn I, Dra I, and Mlu I. To accurately map Tn5 insertions within each restriction fragment, selected pTFX1::Tn5 plasmids were cleaved with Hpa I, an enzyme with two symmetrical restriction sites within the inverted repeat sequence elements of Tn5. Hpa I has two restriction sites in pTFX1. This enzyme was used for this purpose rather than Bgl II since there are no Bgl II restriction sites in pTFX1. Plasmid DNA was electrophoresed in 0.6% agarose at 100 v. For the separation of fragment sizes greater than 15 kb, field inversion electophoresis was used. At 0.3 s intervals, the electric field was inverted between 100 v toward the anode and 60 v toward the cathode. Field inversion gels were run for 16 hours at 4° C. All gels were 10 cm in length.

The ability of a strain to produce trifolitoxin was determined by bioassay; Southern analysis was determined with biotinylated probes of either pLAFR3 or pTFX1; and trifolitoxin was partially purified from the cell culture supernatants of T24 and various Rhizobium transconjugants containing pTFX2 by reverse phase chromatography; these steps all being done as described in the general technique portion of E. riplett, 85 P.N.A.S. USA 3810–3814 (June, 1988) (not prior art).

For example, a bioassay for trifolitoxin appearing at page 3811 of that article is as follows:

A suspension of a trifolitoxin-sensitive strain of *R. leguminosarum* bv. *trifolii* in water was diluted to an OD of 0.1 at 600 nm, and 0.1 ml was spread on 100 mm (maximum diameter) plates containing BSM agar. A sterile cork borer was used to cut a 8 mm diameter hole in the center of the agar. In this hole was placed 100 μl of filter-sterilized culture fluid supernatant or a partially purified sample of trifolitoxin.

When screening transconjugants from the genomic library for trifolitoxin production, a suspension of each transconjugant was prepared in water; 5 μl of each suspension was placed on a BSM plate containing tetracycline at 12.5 μg/ml. After 24 hours at 28° C., each plate was sprayed with a suspension of a tetracycline resistant derivative of R. leguminosarum bv. trifolii 2046, which was prepared by conjugating pRK415, a plasmid that confers tetracycline resistance, into 2046. The conjugation was performed with pRK2013 as the helper plasmid. After 36 hours at 28° C., zones of inhibition were observed in strains carrying plasmids that conferred trifolitoxin production.

When screening recombinant or wild-type strains for trifolitoxin production, suspensions of test strains were prepared and diluted to an OD of 0.1 at 600 nm. These were spread (0.1 ml) on BSM plates and allowed to dry for one hour. Suspensions of each trifolitoxin-producing strain were prepared in water and diluted to an OD of 0.5 at 600 nm. Five microliters of each suspension was placed in the center of a dried BSM plate. After 48 hours at 28° C., zones of inhibition were measured.

From this analysis, I determined that my previous estimate of the size of the insert in pTFX1, 24.2 kb was inaccurate. The insert size in pTFX1 is now known to be 29.5 kb.

The restriction analysis showed that two enzymes, Dra I and Mlu I, did not have restriction sites in either Tn5 or tfx. The tfx region resides on a 10 kb Dra I fragment and a 7.5 kb Mlu I fragment. Since tfx is present on a smaller fragment in the Mlu I digest than in the Dra I digest, Mlu I fragments were chosen for subcloning tfx.

SUBCLONING

One mutant of pTFX1 was chosen whose Tn5 insertion was located within the 7.5 kb Mlu I fragment of pTFX1, yet did not affect the expression of trifolitoxin production in Rhizobium. Ligation of the Mlu I fragments from which contains both the intact trifolitoxin production genes and a Tn5 insertion on the same fragment, to the broad host-range vector, pRK415, allows for selection against the other possible ligation products.

An Mlu I digest of plasmid DNA from a pTFX1::Tn5 mutant was blunted with T4 DNA polymerase using techniques described by F. Ausubel et al., Current Protocols In Molecular Biology, John Wiley & Sons, New York (1987). These fragments were ligated to an alkaline phosphatase-treated Xmn I digest of pRK415. The resulting ligated DNA was transformed into DH5a competent cells and transformants selected on LB solid medium supplemented with kanamycin and tetracycline. Restriction analysis of the plasmid DNA of a selected transformant showed an insert size of 13.2 kb (as was predicted based on the size of an Mlu I fragment of pTFX1 with a Tn5 insertion). This plasmid is referred to as pTFX2.

A restriction map of pTFX2 was prepared based on the restriction sites known to be present in pRK415, the Eco RI restriction sites present in the Mlu I fragment in pTFX1, and on double restriction digests of pTFX2 with Sst I, Eco RI, and Hpa I. The Xmn I site in pRK415 and the Mlu I sites in the insert were eliminated by the blunt end ligation of the insert into the vector.

To determine whether pTFX2 possessed functional tfx, this plasmid was conjugated into Rhizobium. Trifolitoxin production was observed by the resulting transconjugants and confirmed using techniques described previously for pTFX1 transconjugants in E. Triplett 1988, sucra (not prior art).

INSERTION INTO BACTERIAL GENOME

As an example of inserting tfx into a selected bacterial genome, the method of G. Ditta, 118 Meth. Enzmol. 519-528 (1986) was adapted for R. leguminosarum bv. trifolii TA1. (A. Gibson, CSIRO) The technique starts from the idea that certain plasmids may be incompatible with certain other plasmids in certain hosts, and that under antibiotic stress the host will tend to either drive one out (or hopefully where homology exists take in the unwanted genetic material as part of the bacterial genome). The incompatible plasmid pPH1JI (J. Beringer, 276 Nature 633-634 (1978)) was conjugated into several TA1 transconjugants with my pTFX1::Tn5. It will be appreciated that the host Rhizobium can be other "superior" hosts of interest. The conjugation was interrupted on BSM prepared in noble agar and supplemented gentamycin, kanamycin, and spectinomycin. The resulting exconjugants (with the gene in the cell genome) were replica-plated on BSM with tetracycline. The tetracycline-resistant strains were discarded.

Bacterial strains T24, TA1 (pTFX1), and trifolitoxin-producing TA1 (pTFX1::Tn5) transconjugants and TA1::TFX::Tn5 exconjugants were streaked to single colonies on BSM medium in the absence of selective antibiotics. After two days of incubation at 28° C., a portion of the confluent growth on the plate was suspended in water and 5 ul of that suspension spotted in the center of a BSM plate for the assay of trifolitoxin production. A single colony from the initial plate was used to inoculate a second plate. After two days, confluent growth on the second plate was used to assay trifolitoxin. The assays continued for 10 "generations" or until trifolitoxin production was no longer observed. TA1::TFX:Tn5 showed stability through ten generations.

It will be appreciated that the present invention involves, inter alia, the location of the trifolitoxin production and resistant genes, the cloning of them, and the development of a way to insert them permanently in the bacterial genome.

Cultures of pTFX1::Tn5 (a/k/a pTFX1:10-15) in E. coli and Rhizobium TA1::TFX:Tn5 (a/k/a TA1::10-15) are on deposit at the American Type Culture Collection, Rockville, Md., U.S.A., with ATCC numbers 67990 and 53912 respectively. They will be made available upon issuance of this patent and as provided under U.S. and other applicable patent laws. However, this availability is not to be construed as a license to use the invention.

The preferred way to use the preferred bacteria is to streak the deposited TA1::10-15 on BSM solid AGAR and wait for 2-3 days. One then streaks the growth product into BSM liquid broth. After several more days one can pour the liquid broth on peat and uses the peat as a carrier to surround the seeds or roots. Note also that other known commercial inoculant techniques can readily be adapted for use with these bacteria. See e.g. R. Roughley et al. in Nitrogen Fixation In Legumes, p 193-209 (1982); resulting in inoculants and inoculated seeds. This invention appears most likely to be useful on clover, peas, beans, vetch, and soybeans, but may well have utility wherever Rhizobium created nodules.

Another possible use of the invention is to insert only the resistance gene in a bacteria and then add trifolitoxin to the soil (or transform a plant cell so it produces the trifolitoxin). In this regard, several vectors are already known that can expressibly transform a plant genome, and many commercial production hosts are known.

It will be appreciated that various other changes to the preferred embodiment may be made. For example, various other strains besides T24 may produce trifolitoxin, and thus their sequences could be used (e.g. after location with a hybridization probe based on pTFX1). Also, means of inoculating the roots of live plants (as opposed to just seeds) during transplantation can easily be developed using known techniques. Further, other means for inserting the foreign genes in the bacterial chromosome may prove useful. See e.g. G. Barry, 4 Bio/Technology 446–449 (1986) and 71 Gene 75–84 (1988). The claims should therefore be looked to to judge the full scope of the invention and the preferred embodiment is not to be considered as representing the full scope of the invention.

I claim:

1. A recombinant Rhizobium bacterium that is capable of assisting in the formation of nitrogen fixation nodules on at least some plants, the bacterium having a foreign DNA sequence inserted in its natural bacterial genome expressively coding for trifolitoxin production, the foreign DNA sequence also coding for resistance to trifolitoxin, said trifolitoxin being a rhizobial proteinaceous material that is encoded for by a nucleotide sequence present in a 4.4 kb DNA fragment of *R. leguminosarum* bv. *trifolii* T24 that is in a pTFX1 portion of ATCC 67990, and said DNA sequence coding for resistance to trifolitoxin having a nucleotide sequence that is present in said 4.4 kb DNA fragment of *R. leguminosarum* bv. *trifolii* T24 that is in a pTFX1 portion of ATCC 67990, wherein the bacterium is selected from the group consisting of *Rhizobium leguminosarum*, *Rhizobium fredii*, and *Rhizobium meliloti*.

2. A recombinant *Rhizobium bacterium* that is capable of assisting in the formation of nitrogen fixation nodules on at least some plants, the bacterium having a foreign DNA sequence inserted in its natural bacterial genome coding for resistance to trifolitoxin, said trifolitoxin being a rhizobial proteinaceous material that is encoded for by a nucleotide sequence present in a 4.4 kb DNA fragment of *R. leguminosarum* bv. *trifolii* T24 that is in a pTFX1 portion of ATCC 67990, and said DNA sequence coding for resistance to trifolitoxin having a nucleotide sequence that is present in said 4.4 kb DNA fragment of *R. leguminosarium* bv. *trifolii* T24 that is in a pTFX1 portion of ATCC 67990, wherein the bacterium is selected from the group consisting of *Rhizobium leguminosarum*, *Rhizobium fredii*, and *Rhizobium meliloti*.

* * * * *